(12) United States Patent
Glaser-Seidnitzer et al.

(10) Patent No.: US 8,116,592 B2
(45) Date of Patent: Feb. 14, 2012

(54) METHOD AND USER INTERFACE TO GENERATE AND PRESENT MEDICAL EXAMINATION RESULTS

(75) Inventors: Karlheinz Glaser-Seidnitzer, Fuerth (DE); Johannes Kling, Zurich (CH)

(73) Assignee: Siemens Aktiengesellschaft, Munich (DE)

( * ) Notice: Subject to any disclaimer, the term of this patent is extended or adjusted under 35 U.S.C. 154(b) by 383 days.

(21) Appl. No.: 12/420,105

(22) Filed: Apr. 8, 2009

(65) Prior Publication Data

US 2009/0254848 A1    Oct. 8, 2009

(30) Foreign Application Priority Data

Apr. 8, 2008   (DE) .......................... 10 2008 017 831

(51) Int. Cl.
*G06K 9/32* (2006.01)
*G06K 9/00* (2006.01)
(52) U.S. Cl. ................ 382/293; 382/294; 382/128
(58) Field of Classification Search .......... 382/128–134, 382/293, 294, 295, 305; 345/619, 650, 661
See application file for complete search history.

(56) References Cited

U.S. PATENT DOCUMENTS

| 5,986,662 | A | 11/1999 | Argiro et al. | |
| 6,606,089 | B1 | 8/2003 | Margadant | |
| 2008/0292153 | A1* | 11/2008 | Binnig et al. | 382/128 |

OTHER PUBLICATIONS

"Enterprise Information Access and the User Experience," KNAB et al, IT Professional, vol. 9, No. 1 (2007) pp. 21-26.
Which Graphical Approaches That Should Be Used to Represent Medical Knowledge?), Lamy et al, Studies in Health Technology and Informatics, vol. 116 (2005) pp. 719-724.
"Ordered and Quantum Treemaps: Making Effective Use of 2D Space to Display Hierarchies," Bederson et al, ACM Transactions on that Graphics, vol. 21, No. 4 (2002) pp. 833-854.

* cited by examiner

*Primary Examiner* — Brian Le
(74) *Attorney, Agent, or Firm* — Schiff Hardin LLP

(57) ABSTRACT

A method for generation and presentation of medical examination results of at least one imaging device includes the steps of definition and input of measurement parameters via an input device, generation of spatially resolved image information with the at least one imaging device,) and storage of the image information as a respective image file on a storage medium, and selection of presentation parameters to show at least one of the image files depending on the selected presentation parameters. Selection and presentation of medical data acquired with imaging methods are optimized by the presentation parameters being automatically combined into multiple hierarchically organized groups. Each group of unselected presentation parameters is presented as a series of nested rectangles, wherein each presentation parameter corresponds to a rectangle, and each group of selected presentation parameters is presented as a step pyramid, wherein each presentation parameter corresponds to one pyramid level.

7 Claims, 3 Drawing Sheets

METHOD AND USER INTERFACE TO GENERATE AND PRESENT MEDICAL EXAMINATION RESULTS

BACKGROUND OF THE INVENTION

1. Field of the Invention

The invention concerns the generation and presentation of medical examination results that have been acquired with imaging methods, and in particular a method and a user interface to generate and present medical examination results.

2. Description of the Prior Art

Doctors, care personnel and administrators must regularly access various data (for example radiological image series, findings, laboratory reports). In software systems for the recording and presentation of medical data (for example the "Radiological Information System", "Picture Archiving System", "Hospital Information System", "Laboratory Information System"), data are stored in browsers in a simple hierarchical classification and are presented as a tree structure in graphical user interfaces, similar to the case with the graphical user interfaces of many data administration systems.

However, this type of classification is not very flexible since multiple problems can occur in the search for data: the folder structure is unknown, the folder structure does not reflect the preexisting knowledge about the data set, the folder structure was modified (i.e. folders were moved, data was deleted or the like).

The efficiency of the data administration inevitably decreases with increasing complexity of such a data administration, i.e. increase of the number of data sets, increase of the interleaving [nesting] of the data sets, increase of the users accessing the data sets, increase of the data fluctuation. Redundancies can occur, for example when data objects are (accidentally) stored twice.

Moreover, in the search for data the case can occur that data are not recorded in the current system, thus for example the access to laboratory values is rejected. It is also possible that the information that is presented to the user with regard to the desired data set is insufficient in order to locate the data set with justifiable effort.

Therefore, a facet-based classification was proposed in the prior art as an alternative to the conventional structure of the data administration. The concept of facet-based classification assumes the outfitting of every single data object with optimally many relevant properties, what are known as metadata. In contrast to similar metadata-based classification systems such as "tagging" and "folksonomy" (trade names), however, these properties are predefined and are in turn subdivided into hierarchies. The sub-division into continent, country, city, district or into company, department, work area, business division, line of business, department, term can serve as an example. Multiple parameters or hierarchies ("facets") can be searched for simultaneous, in an arbitrary order and with an arbitrary degree of detail in the search for a data object.

A disadvantage of this approach relative to the known, simple hierarchical folder structure is that the concept is new to the user and is therefore unfamiliar.

SUMMARY OF THE INVENTION

An object of the present invention is to optimize the selection and presentation of medical data acquired with imaging methods, wherein the user should be cognitively unburdened to the greatest extent possible.

According to the invention, data objects of medical information systems are classified in a "facet-based" manner (multiple hierarchies) and presented on the screen of a graphical user interface. A "facet" can be considered as a group indicator that represents a group of presentation parameters of the data objects. The group indicator is variable, meaning that it is always associated with the parameters respectively hierarchically subordinate to it. The user can establish the presentation parameters singly or in groups. For this the presentation parameters are displayed on the screen. The display of the presentation parameters is based on the metaphor of multiple step pyramids, wherein the basis of each pyramid (i.e. the lowermost step of the pyramid) symbolizes a facet. The steps above this are the respective next hierarchical levels of the respective facet. The step pyramids themselves are designated as "facetamids". Unselected facets or, respectively, facetamids (pyramids) and their facet planes or, respectively, pyramid levels are presented as rectangles in the lower region of the user interface, which corresponds to a "bird's-eye view" of the pyramids. In contrast to this, selected facets are presented in a perspective view as facetamids (for example from a bird's-eye perspective or isometrically) in the upper region of the user interface.

If the user of the graphical user interface selects a facet or directly selects a facet plane with the aid of an input device such as a mouse or the like, the facet is applied as a filter to the available data objects. Facets and facet planes that contain no data objects are masked out; newly selected facets are shifted into the upper region of the user interface relative to other, already "active" facets.

Individual data objects are advantageously also shown in the upper region of the user interface when sufficient space is present on the user interface. This space can be achieved, for example, by limiting the search in that facets are selectively selected and therefore other facetamids or, respectively, planes are masked out.

A descriptive metaphor in which facets presented as step pyramids mnemonically assist the user, and in fact independently of the type of user interface, is thus achieved with the invention for a radiological information system in the form of a facet-based classification.

The method according to the invention for generation and presentation of medical examination results is implemented via a user interface of at least one imaging device with the following steps. Measurement parameters are defined and entered via an input device of the user interface. Spatially resolved image information is generated by the at least one imaging device. Depending on the measurement parameters and storage of the image information, as a respective image file on a storage medium; of presentation parameters are selected to show at least one of the image files on a screen of the user interface dependent on the selected presentation parameters. The presentation parameters are combined into multiple hierarchically organized groups, and each group of unselected presentation parameters is presented as a series of nested rectangles. Each presentation parameter corresponds to a rectangle, and each group of selected presentation parameters is presented as a step pyramid, wherein each presentation parameter corresponds to one pyramid level.

Preferred embodiments of the method according to the invention exhibit one or more of the following features:

- a presentation parameter with great importance is shown as a lower pyramid level or, respectively, large rectangle, and a presentation parameter with lower importance is shown as an upper pyramid level or, respectively, small rectangle;
- the edge length of a pyramid level or, respectively, of a rectangle on the screen is dependent on the number of image files whose presentation parameters coincide with the selected presentation parameters;
at least two pyramid levels are shown;
multiple step pyramids can be shown next to one another;
individual image files can be presented on the screen in addition to the step pyramids.

The corresponding user interface according to the invention of at least one imaging device for generation and presentation of medical examination has an input device for the input of measurement parameters and for the selection of presentation parameters to present image information on a screen of the user interface depending on multiple selected presentation parameters. The user interface also has a storage medium to store spatially resolved image information as a respective image file that was generated with the at least one imaging device depending on measurement parameters, and a display screen to show the image information depending on the selected presentation parameters. The interface further has a control unit to assemble the presentation parameters into at least one hierarchically organized group and that causes presentation of each group of unselected presentation parameters at the display screen as a series of nested rectangles, wherein each presentation parameter corresponds to a rectangle, and that causes presentation of each group of selected presentation parameters as a step pyramid, wherein each presentation parameter corresponds to one pyramid level.

The method according to the invention and the user interface according to the invention with facet-based search have, among other things, the following advantages. The search is more flexible since the user can freely select the criteria of his search and their order. The user immediately receives a feedback from the system during his search and can adapt the search in that he adds additional filters, cancels filters or exchanges them. The facet-based classification of data corresponds more closely to human thinking than a hierarchical tree representation. Evaluations and sortings of data according to specific criteria can be generated and visualized more easily.

DESCRIPTION OF THE PREFERRED EMBODIMENTS

Figure 1:
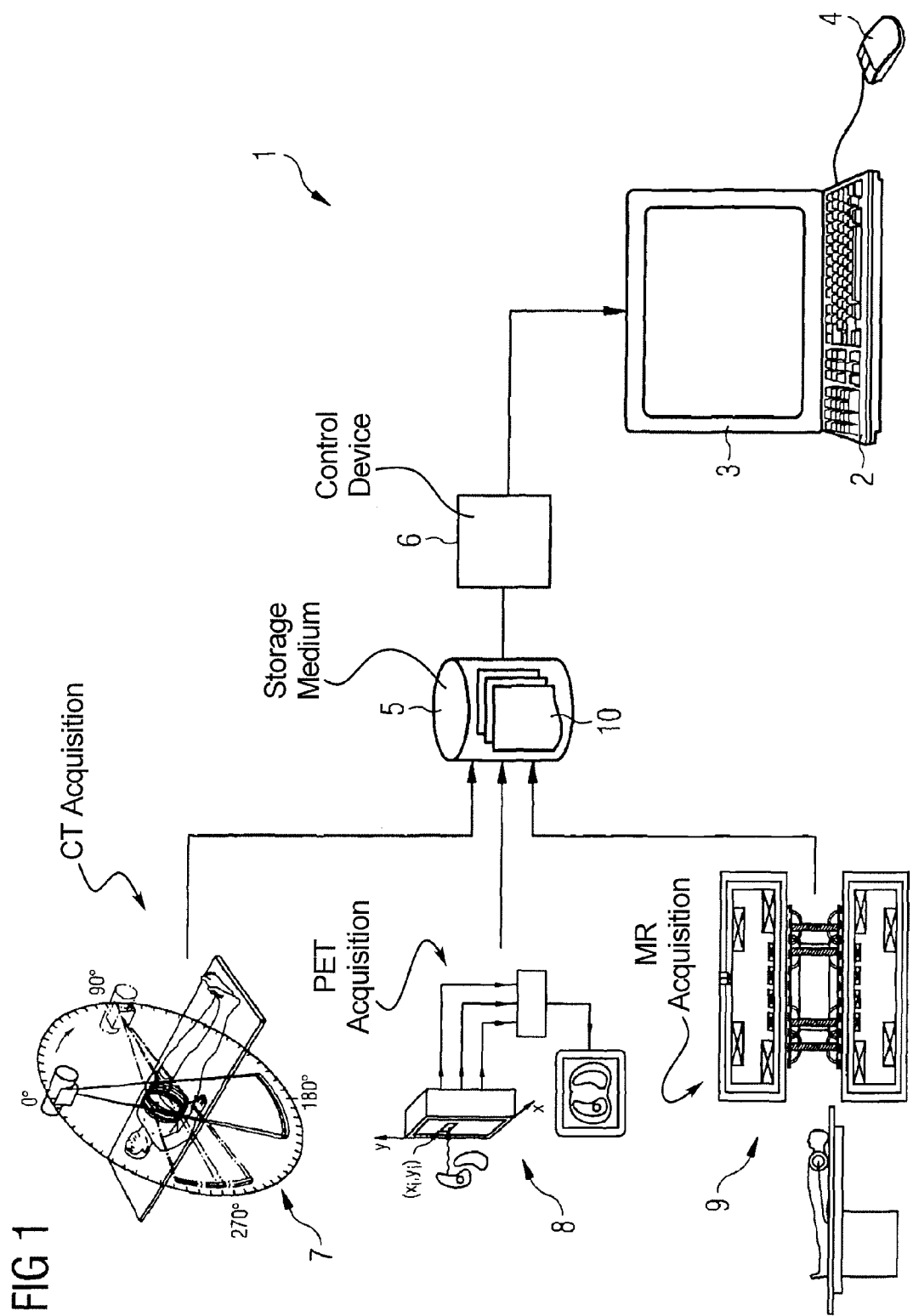
FIG. 1 schematically shows the design of an embodiment of the user interface according to the invention.

FIG. 1 shows an embodiment of user interface 1 according to the invention. The user interface 1 has an input device 2 for the specification of measurement parameters by the user. This interactive setting of the measurement parameters as well as the measurement result are displayed on a screen 3 of the user interface. The user is assisted in the setting of parameters and in the selection of parameters or, respectively, shown objects by an electromechanical converter, for example what is known as a computer mouse 4 or what is known as a "trackball" (not shown) or other suitable devices.

In a pure display function of the user interface 1, data are retrieved from a storage medium 5 and then displayed on the screen 3. The data are present on the storage medium as files 10 that, for example, contain all image information of an exposure with established measurement parameters. If a measurement parameter is changed and the acquisition is repeated with the modified measurement parameters, a new image file 10 is automatically created. The display of the image information in an image file 10 on the screen 3 of the user interface 1 is thereby controlled by a special control device 6.

The data on the storage medium 5 that are displayed on the screen 3 at an arbitrary point in time were acquired with one of three imaging methods and exist as a result of a computed tomography (CT) acquisition 7, or as a result of a positron emission tomography (PET) acquisition 8, or as a result of a magnetic resonance (MR) acquisition 9. Two methods can also be combined with one another, for example PET and CT into PET-CT.

The data from one or more of the imaging methods 7, 8, 9 indicated in FIG. 1 are displayed on the screen 3. The display of the data depends on preset display or presentation parameters. The presentation parameters can in principle be selected independently; their number is also not predetermined beforehand. Under the circumstances, a great many parameters must thus be checked as to whether they must be varied or not. As a result of this it is desirable to display the presentation parameters clearly and therefore as hierarchically as possible and organized according to themes. An optimally comprehensive overview should be presented to the user in that as many parameters as possible are simultaneously displayed.

Figure 2:
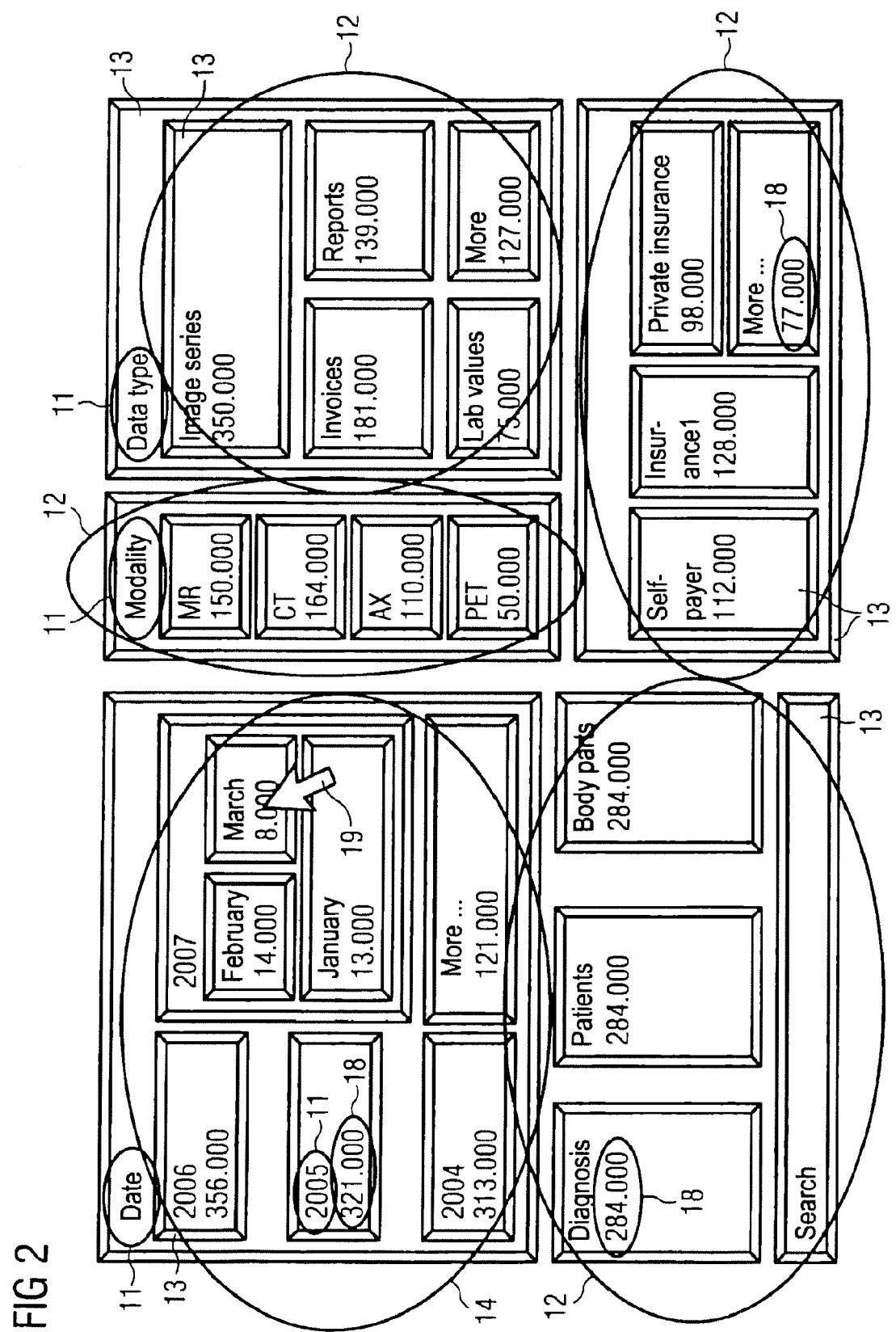
FIG. 2 shows an example of a two-dimensional display of presentation parameter on the user interface according to the invention.

In the facet-based presentation of the parameter space according to FIG. 2, the type of the measurement (MR, CT, PET etc.), the type of the data in the file (image information, remote associated text files such as invoices, reports etc.) or information regarding the patient (insurance, personal information, primary care physician etc.) are also displayed as parameters regarding an image file in a hierarchical but nevertheless optimally complete presentation on the screen 3, except for the date of the measurement. In FIG. 2 this corresponds to the themes "Date", "Modality", "Data type", "Diagnosis", "Patients", "Body parts" and "Insurance" that are shown are respective separate presentation parameters 11.

If the physician or medical personnel would like to have image information regarding a specific patient and a specific examination that was conducted on the patient displayed in a large data bank, at least one of the cited parameters must be set; the others can remain undefined under the circumstances. Given selection of the parameter 11 ("Modality"), the user can thus select whether he would like to view data acquired with MR or data acquired with CT. Given "Data type" as a presentation parameter 11, the user can establish whether he would like to view invoices or reports. These parameters 11 and their respective specific switches are presented in the form of rectangles 13. The rectangles are nested so that the parameters or switches with high importance essentially form the base, and those parameters or switches with low importance that can only be set in a second or third step "grow" upwards and therefore represent rectangles 13 further inward.

If the user would like to set a specific set of parameters and predetermine them for the display of files, he selects the corresponding group of parameters via activation of the respective presentation parameter 11 (for example by "clicking" with a computer mouse) when a pointer symbol 19 is located over the selected parameter 11 on the screen 3. The control unit to control the presentation on the screen 6 therefore recognizes that the corresponding group should therefore be activated and modifies its presentation on the screen 3, as will be explained in the following. The other, unactivated groups can also be unaffected by the modification of the presentation. In FIG. 2 the unactivated groups are designated with 12; in the shown example the activated group 14 is the "Date" group with which it can be checked which data have been generated on a specific day.

Moreover, there are still general selection possibilities (for example "Search") in which the user can input search terms in a more flexible manner. Parameters that are not displayed on the screen for reasons of clarity but whose group is already presented can be retrieved via "More . . . " selection buttons.

In the following a scenario is laid out in which the treating physician or, respectively, the clinical personal wish to check what measurements or, respectively, data and files have been generated on a specific date. In FIG. 2 the pointer symbol 19 therefore stands over the presentation parameter 11 with the designation "Date". The parameters hierarchically subordinate to "Date" pertain to the years "2004" through "2007", and given a prior selection of "2007" the first months "January", "February", "March". Additional months can be recalled with the button that is designated "More . . . ". In this manner an additional specification of the sought data is possible with selection of the presentation parameter 11.

In a preferred embodiment of the method, a number 18 of the data sets that have this parameter value is displayed under the respective parameter. In particular, the size of the presentation of the parameter designation is made dependent on the number 18, which is explained in detail further below.

Figure 3:
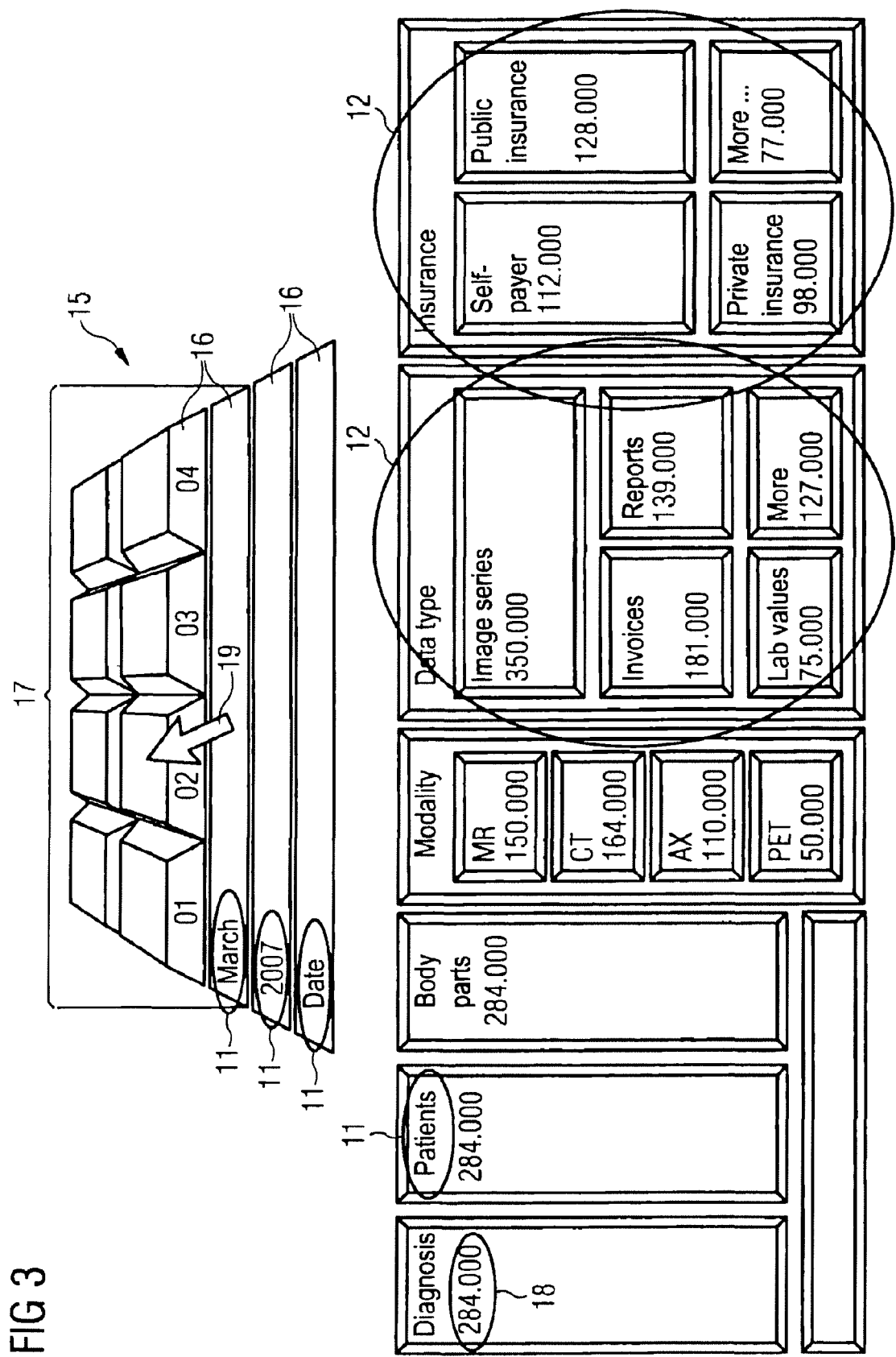
FIG. 3 shows an example for the presentation according to the invention of presentation parameters simultaneously in two- and three-dimensional form on the screen of the user interface according to the invention.

However, since the clarity of the presentation is unnecessarily limited when it is limited to just the two-dimensional representation, according to the invention the presentation of the activated group is transformed into a quasi three-dimensional representation, which is explained in the following using FIG. 3.

When the user activates one or more of the displayed groups as described above, the activated groups or facets are visualized on the entire available screen area of the screen 3 as step pyramids 15—the eponymous facetamid. The pyramid 15 comprises a base level 16 that is designated with the group indicator itself (thus "Date" in the example in FIG. 3). The upper steps represent additional hierarchy levels. In the example according to FIG. 3, the selected year "2007" is a second level 16. A third level 16 is the month "March", and finally the uppermost level 16 contains the individual days of the month. The sizes of the respective levels 16 on the screen 3 are advantageously dependent on the scope of the represented data, thus dependent on the number of matches in a level 16. The number of data contained in the level can thus be estimated using an edge length 17. In contrast to this, in the rectangle presentation of the unactivated or, respectively, unselected groups 12 with multiple nested rectangles 13 that is explained above, the number of represented data or, respectively, image files is indicated as a number 18 under the parameter 11 that stands for the rectangle 13. Two hierarchy levels of a pyramid 15 are always advantageously shown.

Given a partial activation of parameter groups, there is thus a heterogeneous presentation of the parameters on the screen 3. Parameter groups 12 that were not selected are presented at the bottom of the screen 3 as nested rectangles 13 in the shown embodiment, thus as if a pyramid is viewed from a bird's-eye perspective. In contrast to this, a selected parameter group 14 is shifted into the upper region of the screen 3. It is somewhat rotated so that the impression of a perspective view results. Naturally, multiple groups 14 are activated and presented in parallel. In the pyramids as active groups 14 the user can subsequently conduct additional selection procedures by means of pointer symbol 19.

The following advantages relative to a simple hierarchical taxonomy result with this presentation of the parameters or, respectively, facets by means of user interface or, respectively, facetamid interface:

1. The search is more flexible since the user can select the criteria of his search and its order himself.

2. During his search the user thus receives a feedback from the system and can adapt the search in that he adds additional filters, cancels filters or exchanges them.

3. The facet-based classification of data corresponds more closely to human thinking than a hierarchical tree representation.

4. Evaluations and sortings of data according to specific criteria can be easily generated and visualized.

In everyday work, text-based or input-based interfaces lend themselves better than the facetamid view too many tasks that contain a facet-based search. This is on the one hand for space reasons since facetamids allow less space for other interface elements. On the other hand, facetamids require a high degree of interaction in the event that no automatic pre-selection of the facets relevant to a search (for example task- or user-specific facets) can occur.

However, the use of facetamids is very reasonable given specific tasks that are best conducted in a visually optimized environment (browsing, facet-based statistical evaluation). Independent of the regular use, facetamids have yet another advantage: the graphical visualization of facets as step pyramids provides the user with a visual conception of the mode of operation of facets. This mental model is important. A user can also then easily remember and reproduce [actions] when he works directly with a different facet-based interface.

Facetamids thus establish a mental model and are particularly reasonable as an assistive user interface when it can be used by the user for more complex tasks or visualizations.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating and presentation of medical examination results at a user interface of an imaging device, comprising the steps of:
   via an input device of the user interface, defining measurement parameters and entering the defined measurement parameters into the imaging device;
   in a processor of said imaging device, automatically generating spatially resolved image information, dependent on the defined measurement parameters and stored image information that is accessible by said processor, to generate an image file on a storage medium;
   via said input unit of said user interface, selecting presentation parameters to cause at least one of said image files to be displayed at a display screen of the user interface depending on the selected presentation parameters; and
   in said processor, combining the presentation parameters into multiple, hierarchically organized groups, and presenting each group of unselected presentation parameters as a series of nested rectangles at said display screen, with each presentation parameter corresponding to one of said rectangles, and at said display screen, said processor causing each group of selected presentation parameters to be shown corresponding to one level of a pyramid.

2. A method as claimed in claim 1 comprising, in said processor, causing a presentation parameter with a high importance to be shown at a lower pyramid level, or as a large rectangle, and causing a presentation parameter with a lower importance to be shown as an upper pyramid level, or as a smaller rectangle.

3. A method as claimed in claim 1 comprising, in said processor, setting an edge length of a pyramid level, or an edge length of a rectangle, at said display screen to be dependent on a number of said image files having presentation parameters that coincide with the selected presentation parameters.

4. A method as claimed in claim 1 comprising, in said processor, causing at least two pyramid levels to be shown at said display screen.

5. A method as claimed in claim 1 comprising, in said processor, causing multiple step pyramids to be shown next to teach other at said display screen.

6. A method as claimed in claim 1 comprising, in said processor, causing individual image files to also be shown at said display screen in addition to said pyramid.

7. An imaging device for generating and presentation of medical examination results at a user interface comprising:
 an input device of the user interface, allowing defining of measurement parameters and entry of the defined measurement parameters into the imaging device;
 a processor in said imaging device, configured to automatically generate spatially resolved image information, dependent on the defined measurement parameters and stored image information that is accessible by said processor, to generate an image file on a storage medium;
 said input unit of said user interface, being configured to allow entry of presentation parameters to cause at least one of said image files to be displayed at a display screen of the user interface depending on the selected presentation parameters; and
 said processor being configured to combine the presentation parameters into multiple, hierarchically organized groups, and present each group of unselected presentation parameters as a series of nested rectangles at said display screen, with each presentation parameter corresponding to one of said rectangles, and at said display screen, said processor causing each group of selected presentation parameters to be shown corresponding to one level of a pyramid.

* * * * *